United States Patent [19]

Pike et al.

[11] Patent Number: 5,009,251

[45] Date of Patent: Apr. 23, 1991

[54] FLUID FLOW CONTROL

[75] Inventors: Kelly A. Pike, Laguna Hills; Stephen R. Hessel, Fountain Valley, both of Calif.

[73] Assignee: Baxter International, Inc., Deerfield, Ill.

[21] Appl. No.: 271,730

[22] Filed: Nov. 15, 1988

[51] Int. Cl.[5] ............................................. F16K 11/16
[52] U.S. Cl. ................................ 137/601; 137/561 A; 137/636.1; 604/246
[58] Field of Search .................. 137/599, 601, 636.1, 137/607, 863, 597, 561 A, 861; 604/246; 251/10, 9, 7

[56] References Cited

U.S. PATENT DOCUMENTS

| | | | |
|---|---|---|---|
| 954,898 | 4/1910 | Stenberg | 137/863 X |
| 1,964,300 | 6/1934 | Perry et al. | 138/43 |
| 2,236,084 | 3/1941 | Brown | 138/43 |
| 2,289,905 | 7/1942 | Dasher . | |
| 2,323,115 | 6/1943 | Bryant . | |
| 2,376,022 | 5/1945 | Wolcott | 137/636.1 |
| 2,506,179 | 5/1950 | Taplin . | |
| 2,509,456 | 5/1950 | Saballus | 137/599 X |
| 2,511,733 | 6/1950 | Morrison . | |
| 2,519,448 | 8/1950 | Fairchild | 137/636.1 |
| 3,213,333 | 10/1965 | Mikina et al. . | |
| 3,233,457 | 2/1966 | Martinez | 137/208 |
| 3,298,367 | 1/1967 | Bergman | 137/599 |
| 3,378,023 | 4/1968 | Beeken . | |
| 3,398,860 | 8/1968 | Battig . | |
| 3,470,915 | 10/1969 | Bitzer et al. . | |
| 3,532,126 | 10/1970 | Boothe . | |
| 3,532,127 | 10/1970 | Vogelsang et al. . | |
| 3,587,313 | 6/1971 | Smith . | |
| 3,690,318 | 9/1972 | Gorsuch . | |
| 3,785,378 | 1/1974 | Stewart | 251/207 |
| 3,841,354 | 10/1974 | McDonnell | 138/43 |
| 3,877,428 | 4/1975 | Seagle et al. | 604/248 |
| 3,882,892 | 5/1975 | Menzel . | |
| 3,921,916 | 11/1975 | Bassous . | |
| 3,998,427 | 12/1976 | Bentley . | |
| 4,006,753 | 2/1977 | Ingram et al. | 137/607 |
| 4,011,893 | 3/1977 | Bentley . | |
| 4,079,737 | 3/1978 | Miller | 251/207 |
| 4,096,879 | 6/1978 | Serur et al. | 604/246 |
| 4,209,133 | 6/1980 | Mehoudar . | |
| 4,275,767 | 6/1981 | Westfall . | |
| 4,298,000 | 11/1981 | Thill et al. . | |
| 4,300,596 | 11/1981 | Burke . | |
| 4,375,813 | 3/1983 | Hessel . | |
| 4,509,946 | 4/1985 | McFarlane . | |
| 4,518,011 | 5/1985 | Stoll | 137/599 X |
| 4,527,595 | 7/1985 | Jorgensen et al. . | |
| 4,534,757 | 8/1985 | Geller . | |
| 4,537,680 | 8/1985 | Barth . | |
| 4,552,178 | 11/1985 | Olsson . | |
| 4,581,624 | 4/1986 | O'Connor | 357/26 |
| 4,626,244 | 12/1986 | Reinicke | 604/141 |
| 4,634,434 | 1/1987 | Marino, Jr. et al. | 604/245 |
| 4,691,738 | 9/1987 | McCune | 137/597 X |
| 4,696,195 | 9/1987 | Savonlahti et al. | 137/863 X |
| 4,715,852 | 12/1987 | Reinicke et al. | 604/131 |
| 4,756,508 | 7/1988 | Giachino et al. . | |
| 4,822,344 | 4/1989 | O'Boyle | 604/246 X |

OTHER PUBLICATIONS

Cobb et al, Application Ser. No. 692,145, filed Dec. 20, 1967, published Dec. 24, 1968, as noted at 8570.6.1039.

Primary Examiner—Stephen M. Hepperle
Attorney, Agent, or Firm—Knobbe, Martens, Olson & Bear

[57] ABSTRACT

Disclosed is a variable fluid flow controller for regulating the rate of flow from a source of fluid under pressure, comprising a plurality of unique flow restriction passageways, a valve associated with each passageway, and a rotatable cam for selectively opening any one of the valves while maintaining the remaining valves closed. The flow restriction passageway preferably comprises a channel etched on the surface of a first silicon wafer and enclosed by a second wafer to form a fluid flow passageway, one of the first or second wafers having a plurality of apertures therethrough for intersecting the passageway at various distances along its length.

17 Claims, 3 Drawing Sheets

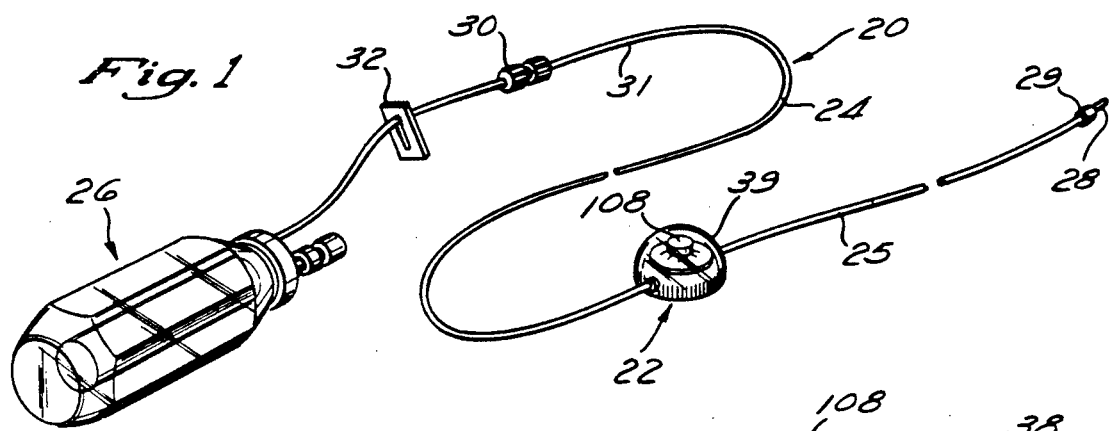
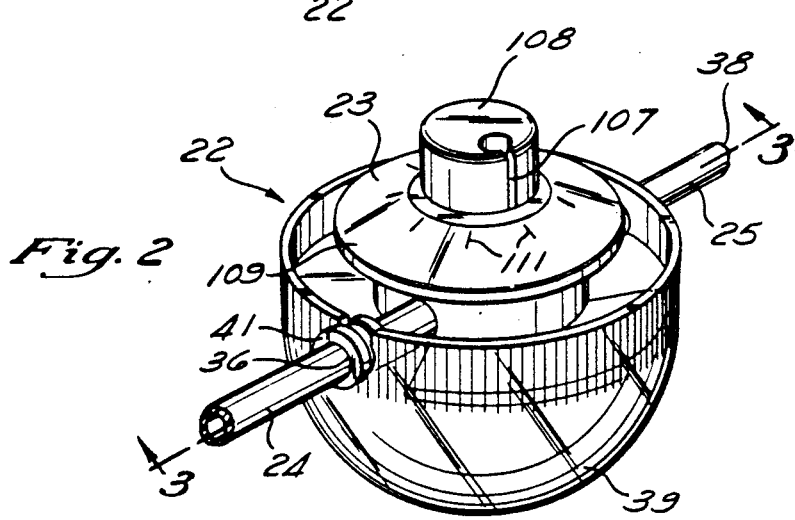
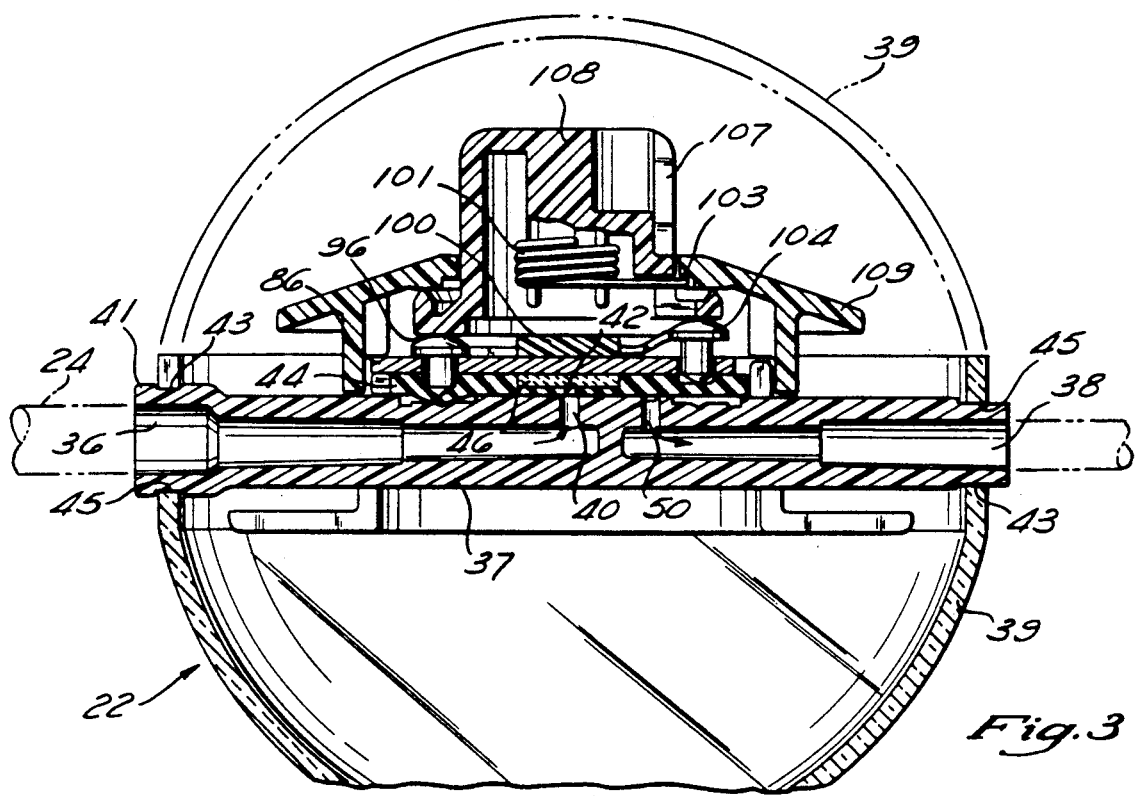

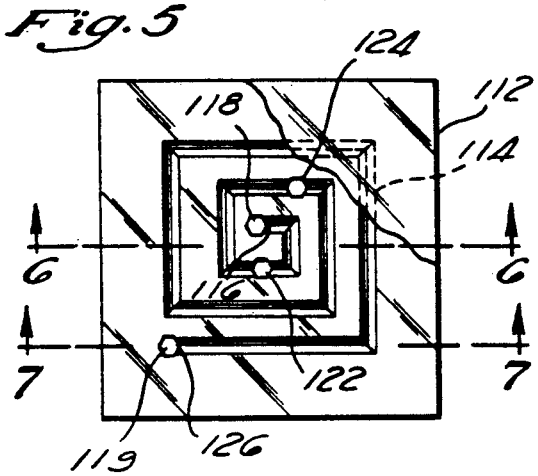
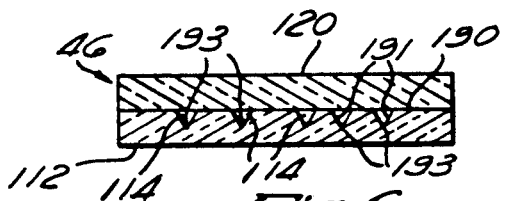
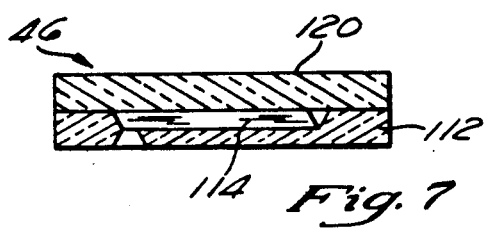
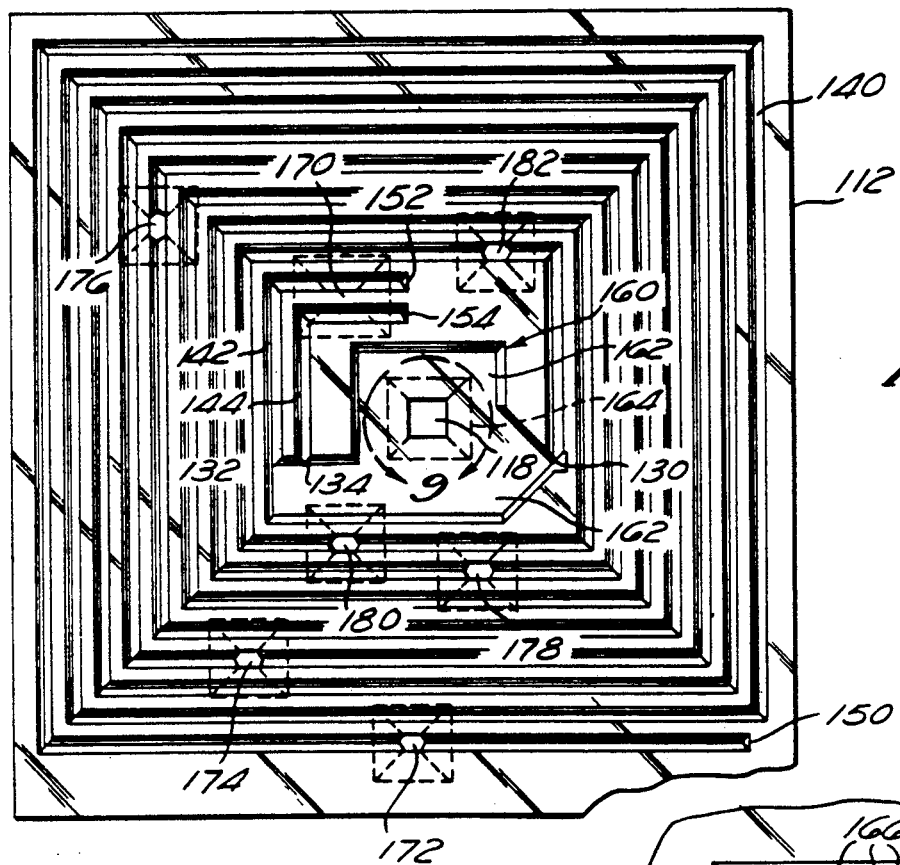
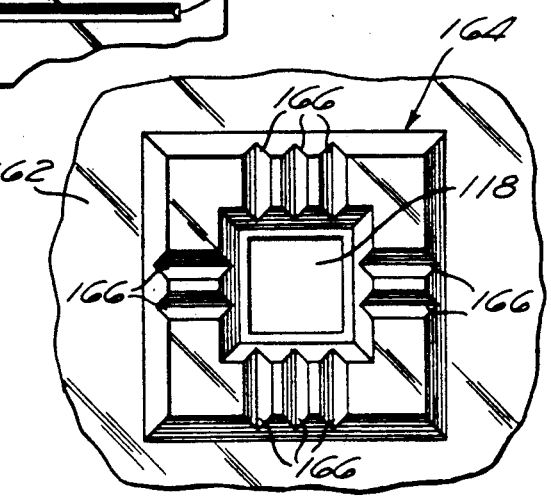

FLUID FLOW CONTROL

BACKGROUND OF THE INVENTION

The present invention relates to medical infusion devices, and, more particularly, to variable flow rate regulators for accurately regulating the effluent flow from a source of pressurized fluid.

Intravenous or other parenteral administration of fluids is routinely performed in hospitals, other medical facilities, and emergency sites in the field. Depending upon the nature of the infusate, it is desirable for the clinician to be able to accurately and rapidly select an appropriate rate of delivery. For example, infusion of normal saline or lactated Ringer's solution to achieve normovolemia during surgery or following trauma is typically accomplished at a relatively high flow rate. On the other hand, administration of certain antiarrythmics such as Lidocaine or Procanamide following myocardial infarction may desirably be accomplished at any of a variety of relatively slow rates. In addition, administration of certain antineoplastic agents must be performed at a very slow and constant rate over a prolonged period to avoid localized necrosis at the infusion site. Even the IV administration of antibiotics is desirable in some circumstances, at relatively slow delivery rates such as 50 cc over 90 minutes or more. Not only do a large variety of situations exist which each require unique flow rates, but it may also be desirable in certain applications to be able to vary the flow rate once infusion has commenced.

A number of flow regulators have been developed from the simple adjustable clamp and counting of drips per minute to elaborate peristolic pump devices. Nonetheless, there remains a need for a variable flow regulator which is accurate, capable of providing any of a number of convenient preselected flow rates, and yet which is inexpensive to produce. In addition, there exists a need for such a device which is compact and simple to use, thereby accommodating the needs in the operating room, in the field, and of the ambulatory patient, while at the same time providing for precise delivery rates with minimal operator error and offering tamper-proof setting of the flow rate. Moreover, there exists a need to be able to quickly and accurately confirm the flow rate setting of the variable flow controller.

SUMMARY OF THE INVENTION

In accordance with one aspect of the present invention, there is provided a variable rate fluid flow controller for providing a predetermined delivery rate from a pressurized source of fluid, comprising a housing having an influent port, an effluent port and at least two flow restriction paths therebetween. At least two valves are provided in the housing, each valve associated with a unique flow path, and a movable cam is provided for selectively opening and closing the valves. The flow paths may be disposed in series or parallel relationship, or may comprise a single length of flow restriction passageway having an influent port and a plurality of effluent apertures disposed along its length.

Each flow path is optimally provided with a pinch valve, which preferably comprises a moveable wall which may be compressed by the cam to prevent fluid flow through the associated flow path. In accordance with one preferred embodiment, a piston is associated with each pinch valve, the piston moveable from a first position in which fluid is permitted to flow through the valve and a second position in which a flexible diaphragm is compressed to prevent fluid flow through the valve, the piston being moveable between the first and second positions in response to the rotational position of the cam.

In accordance with a further aspect of the present invention, there is provided a flow regulator for use with the foregoing variable rate fluid flow controller. The flow regulator comprises a first plate having a flow channel on the surface thereof, and a second plate secured to the surface of the first plate and enclosing the flow channel to form a chip having a capillary tube therethrough. An influent port is provided on the chip in fluid communication with the capillary tube, and a plurality of effluent apertures are provided on the chip, each in fluid communication with the capillary tube at a different distance along its length from the influent port.

Further features and advantages of the present invention will become apparent from the detailed description of preferred embodiments which follow, when taken together with the appended figures and claims.

BRIEF DESCRIPTION OF THE DRAWINGS

FIG. 1 is a schematic representation of an infusion system which incorporates a flow regulator according to the present invention.

FIG. 2 is an enlarged perspective view of a flow regulator according to one embodiment of the present invention.

FIG. 3 is an elevational cross-sectional view taken along the lines 3—3 of FIG. 2, of a flow regulator according to the present invention.

FIG. 5 is a partial cut-away plan view of a simplified flow regulating wafer according to the present invention.

FIG. 6 is an elevational sectional view along the lines 6—6 of the flow control wafer in FIG. 5.

FIG. 7 is an elevational sectional view along the lines 7—7 of the flow control wafer in FIG. 5.

FIG. 8 is an overhead view of the preferred embodiment of the control wafer.

FIG. 9 is an enlarged overhead view of the filter area of the preferred control wafer of the present invention.

DETAILED DESCRIPTION OF PREFERRED EMBODIMENTS

Figure 4:
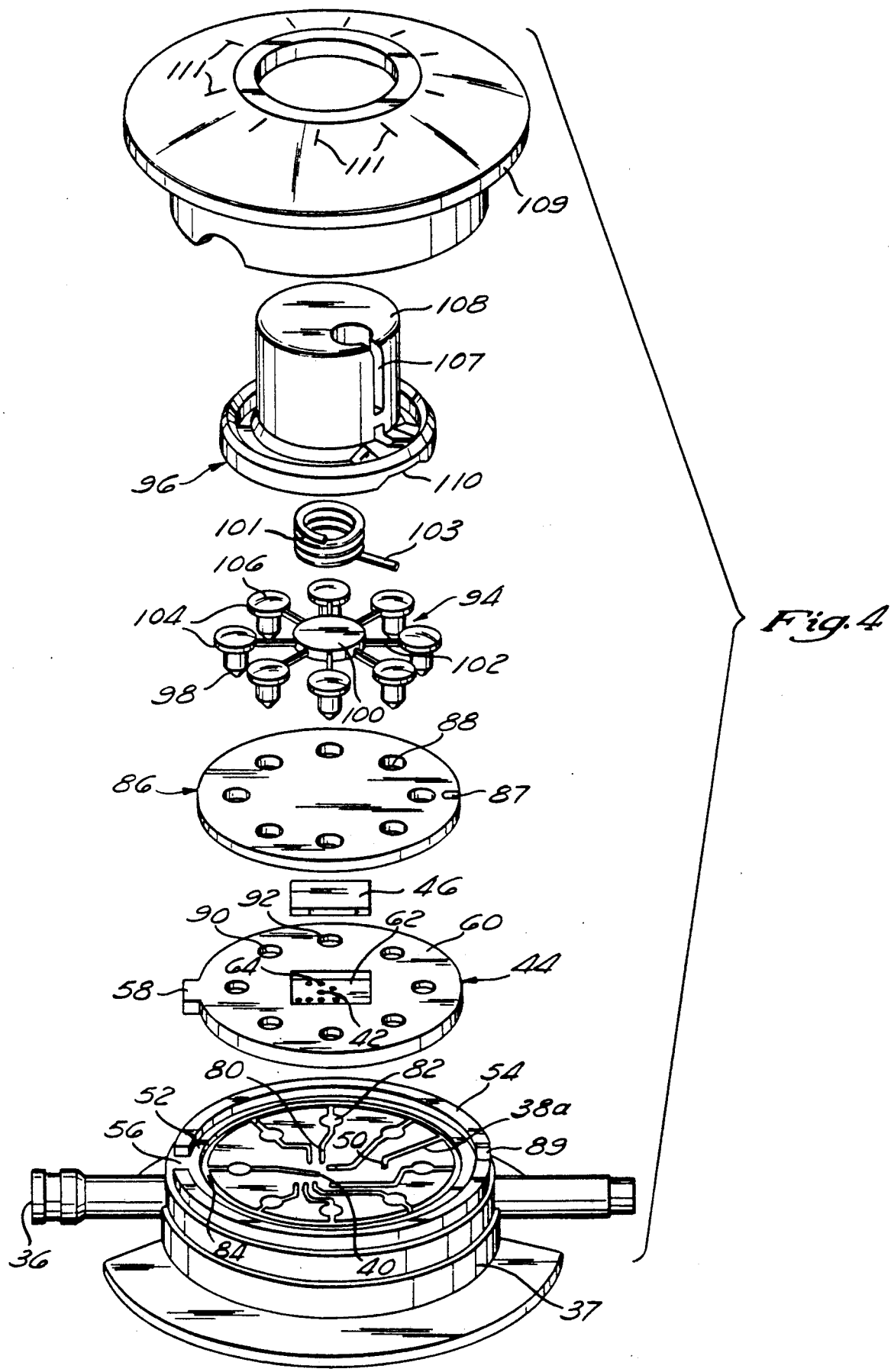
FIG. 4 is an exploded perspective view of the flow regulator illustrated in FIG. 3.

Referring to FIG. 1, there is disclosed an infusion system 20 adapted for delivering a medication or other fluid contained in a source 26 to a patient (not illustrated). The source 26 may be any of a variety of known medication dispensers, from gravity feed IV bags to mechanical pumps. Preferably, however, the fluid source will be a relatively constant pressure delivery system, such as the Intermate ® elastomeric bladder infusion pump disclosed in U.S. Pat. No. 4,769,008 and commercially available from Infusion Systems Corporation of Huntington Beach, Calif.

The infusion system 20 further comprises a flow regulator 22 according to the present invention, in fluid communication with the source 26 by way of standard IV line 24. Fluid is conducted from the flow regulator 22 to a patient by way of IV line 25.

The downstream end 28 of IV line 25 is optimally provided with a standard luer connection 29 or other connector adapted for convenient attachment to an IV needle, piggyback connection, or the like. In addition, to facilitate connection of the flow regulator 22 to a source 26, the upstream end 31 of IV line 24 is provided with a connector 30 which may comprise a luer, snap fit, or other convenient connector known in the art.

FIG. 2 illustrates an enlarged perspective view of the flow regulator 22, provided in accordance with one aspect of the present invention. The flow regulator 22 has a generally circular profile when viewed from an angle normal to the control surface 23. Surface 23 is provided with a selector knob 108 which may be rotated through a series of positions which provide a graduated series of different flow rates. Optionally, an "off" position may additionally be provided for completely interrupting the flow. Relative position of the knob 108 may be determined by reference marker 107 which may comprise a painted stripe or groove.

Extending radially outwardly from the knob 108 is an annular flange 109. The annular flange 109 is optimally provided with indicial markings 111 which correspond to the different flow rates of the regulator 22.

The influent channel 36 and the effluent channel 38 are conveniently coaxially aligned so that they may function as pivots for transparent cover 39. For this purpose, a collar 41 is provided on each of channels 36 and 38, each collar 41 having an annular recess 43 for engaging an aperture 45 in cover 39. In this manner, cover 39 may conveniently be pivoted to expose knob 108 for selection of a flow rate, as shown in FIG. 2, and then pivoted back to cover knob 108 and protect against accidental readjustment.

Cover 39 is thus optimally molded from any of a variety of rigid thermoplastic materials such as acrylic or styrene, which are substantially transparent to visible light to permit viewing of the selected flow rate. Optionally, cover 39 may be provided with a locking means for preventing access to control knob 108 once cover 39 has been rotated into position.

By incorporating a transparent housing that rotates to cover the settings, the present invention provides for the ready visual confirmation of the settings. In addition, the transparent housing may be permanently or temporarily locked in its protective position to prevent intentional or unintentional tampering with the setting.

Referring to FIG. 3, the cover 39 is shown in its protective configuration in phantom, and influent IV line 24 (shown in phantom) terminates in an influent channel 36 in the base 37 of flow regulator 22.

IV line 24 may be secured in fluid communication with influent channel 36 by an adhesive, friction fit, or by mechanical locking structures such as a luer lock, as may be desired depending upon the intended use. Preferably, the flow regulator will be provided with a short length of a connection line 24 which is secured to influent channel 36 by an adhesive material such as a quantity of a urethane-based UV cured epoxy or other material that will be substantially inert in the presence of a pharmaceutically active material to be dispensed through the flow regulator 22.

Although many physical configurations would be adaptable for use with the present invention, the base 37 preferably comprises a radially symmetrical body such as a generally cylindrical body, best illustrated in FIG. 4. All of the additional major components of the flow regulator 22, including the gasket 44, the valve guide 86, the hub 100, the knob 108, and flange 109 are also preferably substantially radially symmetrical about a common axis perpendicular to the axial end surface of the base 37. This configuration facilitates convenient operation of a rotational control, such as knob 108, as will be discussed.

Base 37 may be formed in any of a variety of methods well known in the art, such as by injection molding of a thermoplastic resin. Selection of materials is not critical, as long as the components of the flow regulator are comprised of, or coated with, a material which is substantially inert in the presence of the medicinal fluid to be conducted therethrough. For example, acrylic or styrene are generally well suited for this purpose.

Referring to FIGS. 3 and 4, fluid from the source 26 is driven through IV line 24 and into channel 36. Channel 36 communicates with an influent port 40, which, in the illustrated embodiment in FIG. 3, is perpendicularly disposed to the longitudinal axis of channel 36. Port 40 terminates at an interface between the upper surface of base 37 and an adjacent gasket 44.

Fluid exiting port 40 passes through a coaxially aligned aperture 42 in the gasket 44. The gasket 44 is preferably formed from an elastomeric material which exhibits good resilient sealing characteristics as will be described. Suitable materials for the gasket include known vulcanized synthetic polyisoprenes, as well as natural latex or silicone rubber, or blends of natural and synthetic rubber. Non-rubber gasket materials may also be used, either with a rubber coating or without, provided the gasket is capable of performing its function of sealing the variety of flow passages therethrough.

The gasket 44 can be formed by punching from a stock sheet and boring or etching or drilling such as by mechanical drill or by laser to produce the apertures and depressions contained thereon; or by known molding processes as will be appreciated by one skilled in the art. Since portions of the gasket will be in contact with the medicinal fluid delivered through the flow regulator, at least those portions (e.g., the interior of aperture 42) should be composed of, or coated with, a material which will exhibit suitable stability for that purpose.

Although any of a variety of configurations may be selected, the gasket is preferably radially symmetrical to accommodate the rotational operation of a cam 96 on the lower surface of knob 108, as will be discussed. In the illustrated embodiment as shown in FIG. 4, the gasket 44 is substantially circular in shape so that it will fit within the circular depression 52, on the base 37, formed by an annular flange 54. As shown in FIG. 4, the annular flange 54 is preferably provided with an interruption to form guide 56 for receiving a key 58 extending radially outwardly from the gasket 44 to facilitate manufacturing and to maintain the gasket 44 in proper rotational alignment with the base 37. Although not shown, alternative rotational alignment guides can be used such as one or more apertures on the gasket 44 for receiving corresponding pins extending from the upper surface of the base 37.

The upper surface 60 of the gasket 44 is provided with a shallow depression 62, dimensioned to receive a flow control wafer 46. The influent aperture 42 traverses the gasket 44 in the area of the depression 62 for fluid communication with the control wafer 46. In addition, a plurality of effluent apertures 64 also pass through the gasket 44 in the region of the depression 62, also to provide fluid communication with the control wafer 46.

Referring to FIGS. 5-7, there is disclosed a simplified flow control wafer 46 according to the present invention. The flow control wafer 46 comprises a first plate 112 having a fluid flow channel 114 formed thereon such as by chemical or laser etching techniques. The channel 114 is enclosed by a second plate 120 secured to the grooved surface of first plate 112 to form a wafer 46 having a flow restriction passageway therethrough. First plate 112 in accordance with the present invention preferably comprises silicon, for reasons which will become apparent, although other materials may be used which will accrue the advantages of the invention.

The first plate 112 is preferably rectangular in shape to facilitate handling and manufacturing operations, although other shapes may be utilized if desired. Plate 112 has a thickness of from about 0.2 to about 3 or 4 mm, and preferably from about 0.2 to about 2 mm. The plate thickness should be at least sufficient to permit etching of a flow channel of the desired depth, while still maintaining the structural integrity of the plate for securing to the second plate 120 and mounting in the flow regulator 22.

The fluid flow channel 114, and other flow channels to be described, may be formed in plate 112 in accordance with known techniques. In the preferred embodiment of the present invention, plate 114 is a silicon wafer, and all fluid flow channels are preferably formed thereon by a single operation using semiconductor processing and micromachining techniques such as those described in U.S. Pat. No. 4,626,244 to Reinicke.

The first plate 112, is preferably a single silicon crystal in which a plane 190 is oriented parallel to the surface of the plate 112 in which the flow restriction grooves 114 are to be formed. It has been determined that the use of an anisotropic etchant is advantageous, due to the ability of such etchants to etch at different rates in different directions along the crystal lattice. This characteristic permits formation of sharp edges and corners during the etching process. A variety of suitable anisotropic etchants are known, including hot alkaline solutions such as aqueous potassium hydroxide, aqueous sodium hydroxide, and a mixture of ethylene diamine, pyrocatchol and water, commonly known as EDP.

The inherent etching characteristics of the above etchants in the silicon crystal permit the etching of passageways having different cross-sectional areas by utilizing a mask which leaves exposed areas on the silicon wafer of different widths. Regardless of the starting width, as the etching operation proceeds the sidewalls of the grooves slope inwardly along converging planes 191 of the silicon wafer, to a point of intersection 193 of the planes 191, as will be understood by one of skill in the art. Thus, each groove which is etched to completion is characterized by a sharp V configuration, with all of the wall portions of the grooves sloped inwardly and downwardly at an angle of 54.74° relative to the planar surface 190 of the first plate 112.

Preparation of low velocity flow regions such as the cavity 162, is accomplished by exposing a much wider surface area of the crystal to the etchant than that for the purpose of forming the fluid flow channel 114. Utilizing the above-mentioned anisotropic etchants, flat-bottomed grooves can be formed in a crystal by stopping the etching operation prior to reaching the depth corresponding to the point of intersection 193 of the converging planes 191. Thus, under the same etching conditions, narrow flow restriction passageways can be formed having precise triangular cross-sectional areas due to the convergence of the planes 191, and larger, flat-bottomed areas can be formed by halting the etching process at a depth which is prior to convergence of the planes 191 which correspond to the initial width of the area exposed to the anisotropic etchant.

Optimally, a plurality of silicon first plates 112 are simultaneously formed from a single large silicon wafer. After the etching process, a second plate 120 is preferably secured to the entire wafer, as will be discussed, and the resultant sandwich cut into a plurality of control wafers 46. The wafer may be cut by utilizing a diamond saw, or by laser cutting. In a diamond saw process, a tape is advantageously placed over either the first plate 112 or second plate 120 depending upon which has been provided with the influent port 118 and effluent apertures 122, 124, 126, etc. In this manner, dust produced during the sawing process will not enter the capillary groove network.

The influent port 118 and apertures 122, 124 and 126 may either be mechanically drilled such as by an abrasive vapor blasting technique or they can be laser drilled.

Referring to the representational plan view of FIG. 5, the plate 112 has a dimension in the x-axis direction of within the range of from about 1 to about 20 mm, and the y-axis dimension will typically fall within the same range. Preferably, the plate 112 is approximately square, having an x-axis and y-axis dimension of the same length, from about 4 to 8 mm, although the size may be varied as a matter of design choice to accommodate the desired flow path dimensions.

As shown in FIGS. 6 and 7, a second plate 120 is sealingly secured to the etched surface of the first plate 112, enclosing the flow channel 114 to form a control wafer 46 having a capillary tube therein. Sealing of the second plate 120 to the first plate 112 may be accomplished by electrobonding.

Referring to FIG. 5, a plurality of effluent apertures 122, 124, 126 are formed through the first plate 112, intersecting the capillary tube at various points intermediate the influent port 118 and the downstream end 119. Because the rate of flow of a fluid through a capillary tube is a function of the length of the flow path as will be described, each tap along the flow path will be associated with a different distance from influent port 118, and, hence, a different flow rate.

Thus, as shown in FIG. 5, the flow channel 114 has an upstream end 116, a downstream end 119 and an influent port 118 extending through the first plate 112, for providing fluid communication with aperture 42 in gasket 44. The length of flow channel 114, the overall dimension of the control wafer 46 and the slowest delivery rate of which the system is capable are all interrelated, due to the known relationship of the flow rate through a capillary tube to the capillary tube's cross-sectional area and length. This relationship is mathematically described by Poiseuille's Law, as expressed in the equation:

$$Q = (Pr^4)/8Ln$$

for a capillary having a circular cross-sectional internal area, where Q is the flow rate in cc/sec through the capillary tube, P is the pressure drop through the tube in dynes/cm$^2$, r is the internal radius of the tube in cm, L is the length of the tube in cm, and n is the viscosity in poise. The flow rate through the flow channel 114 is thus a function of the channel's cross-sectional area and the channel's length, each of which can be varied as desired to accommodate manufacturing tolerances or other considerations. Although it is possible to perform a series of calculations to determine precise flow rates based upon flow channel dimensions, it may alternatively be desirable to empirically measure flow rates and optimize dimensions by trial and error.

In order to permit a length of capillary tube which may be greatly in excess of the dimensions of the flow control wafer 46, the flow channel 114 may advantageously be formed into a spiral, doubled back on itself, or any other space conserving pattern. Thus, the pattern illustrated in FIG. 5 is but a simplified representation of the preferred rectangular spiral design of FIG. 8. By simplified, it is meant that while the illustrated channel 114 in FIG. 5 goes through approximately two and one-half complete revolutions, the channel 114 in the preferred embodiment, as shown in FIG. 8, is actually contemplated to have anywhere from about 1 to as many as about 30 revolutions or more, depending upon the cross-sectional area of the channel and desired rate parameters.

The cross-sectional configuration of the flow channel 114, illustrated in FIG. 6, is essentially triangular as a result of the preferred manufacturing technique. However, other cross-sectional configurations may be utilized without departing from the present invention. In an approximately equilateral triangular configuration, the channel will optimally have side lengths within the range from 0.05 to about 0.2 mm, which equate to a cross-sectional area of within the range of from about 0.002 mm$^2$ to about 0.04 mm$^2$.

Selection of a cross-sectional area for the flow channel may depend upon the desired range of flow rates for the flow regulator 22, the flow channel pattern, and machining or other processing tolerances among other factors. Although there is no theoretical lower limit to the cross-sectional area of the flow passageway, the smaller sizes are more susceptible to blockage and possibly viscosity of the fluid will have a more profound effect so that different medications would behave differently. Similarly, there is no theoretical limit to the maximum diameter or cross-sectional area of the flow channel, except that at a certain point the channel will no longer restrict the flow of fluid to a useful rate for the purpose of the present invention, as will be readily apparent to one of skill in the art.

In the preferred embodiment of the control wafer 46, as shown in FIG. 8, flow channel 140 in first plate 112 is in fluid communication with aperture 42 and influent port 40 of the base 37 (FIG. 3) by means of wafer influent port 118. The first plate 112 of the preferred embodiment of the control wafer 46 also contains a filter area 160, associated with the upstream end of flow channel 140, and also high flow rate channels 142 and 144, as will be discussed.

Referring to FIG. 8, the filter area 160 contains a low velocity cavity 162 and a plurality of influent filter channels 166 as shown enlarged in FIG. 9. Fluid entering the control wafer 146, through the wafer influent port 118 is divided into the plurality of influent filter channels 166. The influent filter channels 166 serve to restrain any foreign matter of size sufficient to block the high flow rate channels 142, 144 or the low flow rate channel 140. It is therefore preferable that the influent filter channels 166 be of the same or, more preferably, of smaller cross-sectional area than the low flow rate channel 140. The number of filter channels 166 is a function of their cross-sectional areas. Optimally, the sum of the areas of channels 166 will be significantly greater than that of flow channel 140, so that the filter does not become a rate limiting structure. Thus, the preferred embodiment is able to trap foreign particulate matter in a filter channel 166 without effecting the desired flow rate.

After passing through the influent filter channels 166, the fluid enters low velocity cavity 162. Cavity 162 functions to manifold the effluent ends of all of the channels 166 for introduction into flow channel 140. In addition, cavity 162 may provide some further filtration due to the reduced velocity therein. Because of the large cross-sectional area of cavity 162 as compared to the cross-sectional area of the low flow rate channel 140 or either of the high flow rate channels 142, 144, the fluid velocity in cavity 162 is substantially less than in flow channels 140, 142, 144. Thus, the low fluid flow velocity in cavity 162 may permit the sedimentation of foreign particular matter which may have passed through the influent filter channels 166.

Referring to FIG. 8, the preferred embodiment is provided with a flow restriction channel 140. Channel 140 is in fluid communication with the cavity 162 by means of a filter aperture 130. The distal end of channel 140 terminates at downstream end 150. Positioned between filter aperture 130 and downstream end 150 are a plurality of apertures 172, 174, 176, 178, 180, and 182. Any one of these apertures 172, 174, 176, 178, 180, and 182 may be selectively fluidly connected to the effluent port 50, as described infra. The apertures 172, 174, 176, 178, 180, and 182 are disposed along the length of the low flow rate channel 140 such that each aperture is disposed at a preselected distance along flow channel 140, and therefore corresponds to a unique, predetermined flow rate.

For example, aperture 172 in a specific embodiment of the present invention is positioned at a flow channel length of approximately 4.05 inches from the filter aperture 130, the flow channel 140 having a cross-sectional area of approximately 0.007 in$^2$. Assuming all other apertures 174, 176, 178, 180 and 182 are closed, the position of the low flow rate aperture 172 provides a flow rate of approximately 1.65 milliliters per hour.

Aperture 174 is positioned at a length of approximately 2.02 inches along channel 140 from filter aperture 130. If all other effluent apertures along flow channel 140 are closed, the position of the low flow rate aperture 174 provides a flow rate of approximately 3.03 milliliters per hour.

Aperture 176 is positioned at a length of approximately 1.35 inches along channel 140 from filter aperture 130. Thereby, the position of the low flow rate aperture 176 provides a flow rate through the aperture 176 of approximately 4.95 milliliters per hour.

Similarly, aperture 178 is positioned at a length of approximately 0.632 inches along low flow rate channel 140 from the filter aperture 130. Thereby, the position of aperture 178 results in a flow rate through the aperture 178 of approximately 10.6 milliliters per hour.

Aperture 180 is positioned at a length of approximately 0.285 inches along channel 140 from aperture 130. The position of aperture 180 provides a flow rate of approximately 23.41 milliliters per hour.

Finally, aperture 182 is positioned at a length of approximately 0.0693 inches along flow channel 140 from the low flow rate channel filter aperture 130. Thereby, the position of the aperture 182 provides a flow rate of approximately 50.0 milliliters per hour. As will be appreciated by one skilled in the art, more or fewer effluent apertures can be provided, at various desired flow rates.

For providing higher flow rates, two or more flow restriction passageways can be coupled in parallel. Thus, in accordance with a further aspect of the present invention, high flow rate channels 142 and 144 are provided in fluid communication with cavity 162 by means of apertures 132 and 134, respectively. The high flow rate channels 142 and 144 terminate at downstream ends 152 and 154 respectively. Positioned between the filter apertures 132, 134 and the high flow rate channel downstream ends 152, 154 is the high flow rate aperture, 170. The high flow rate aperture 170 is in communication with both high flow rate channels 142 and 144.

The high flow rate aperture 170 is positioned a length of 0.0575 inches along the high flow rate channels 142, 144 from apertures 132, 134. The parallel flow arrangement effectively doubles the area of the single flow path to provide a flow rate of approximately 100 mm per hour.

An alternative design (not illustrated) of the control wafer 46 can be constructed having a plurality of discrete flow channels, which may be arranged so that they are substantially parallel to each other, or radiate from a central location. Each discrete channel is provided with an upstream end which is in valved communication with the fluid source, and a downstream end, each of which is conveniently manifolded to a common effluent channel. In this embodiment, rotation of control knob 108 would successively increase or decrease the number of flow paths through which fluid would flow, in series or in parallel as desired, thereby affecting the overall flow rate. In a multiple channel embodiment, the channels could all have the same cross-sectional area, or differing cross-sectional areas can be provided. The valve guide 86, gasket 44 and other components of the flow regular 22 of the present invention can be readily adapted to all of the foregoing variations of control wafer 46.

Moreover, in accordance with a preferred embodiment of the present invention, the flow channel 114 can extend along more than a single surface of plate 112, or along additional plates. For example, flow channel 114 can pass through an aperture (not illustrated) in plate 112 to the backside thereof, which can be provided with a further length of a flow channel. That further channel would be enclosed to form a capillary tube by the addition of a third plate (not illustrated) secured to first plate 112 on the opposite side from plate 120. In this manner, significant design flexibility is permitted by the present invention to accommodate a wide variety of flow restriction channel lengths and designs.

Referring to FIG. 3, when the control wafer 46 is positioned within the depression 62 of the gasket 44, the aperture 42 aligns with the influent port 118 on the control wafer 46. Fluid passing from the influent channel 36 through the port 40 and the aperture 42 will thus proceed to enter the flow channel 140 by way of the influent port 118.

Each of the effluent apertures 172, 174, 176, 178, 180 and 182 along the length of the low flow rate channel 140 and tap 170 of the high flow rate channels 142, 144 is in communication with a corresponding effluent aperture 64 in the depression 62 of the gasket 44 (see FIG. 4). Similarly, each effluent aperture 64 in the gasket 44 communicates with a corresponding flow channel 80 on the surface of base 37. It is to be understood that each of the plurality of flow channels 80 in base 37 function in a similar manner, so that only one need be described in detail herein. Effluent aperture 64 in the gasket 44 is in valved communication by way of the flow channel 80 and the valve chamber 82 with common drain 84 to which each of the plurality of flow channels are manifolded. Thus, fluid exiting channel 140 by way of any of effluent apertures 172, 174, 176, 178, 180 or 182 will pass through a corresponding channel 80 and valve chamber 82 into drain 84. From drain 84, fluid is directed to effluent channel 38 by port 50.

As shown in FIG. 4, in order to form a valve in each of valve chambers 82, a valve guide 86 is disposed on the upper side of the gasket 44. The valve guide 86 may be injection molded or die stamped and drilled as will be appreciated by one of skill in the art. Although it may be convenient to form the valve guide 86 from the same material as base 37, that is not necessary since the material of guide 86 will not contact the medicinal fluid and hence need not exhibit the same level of biocompatibility and chemical stability. In order to maintain the correct rotational alignment, the valve guide 86 is conveniently provided with a notch 87 which engages a pin 89 projecting axially upwardly from annular flange 54 on base 37.

The valve guide 86 contains a plurality of perforations 88 therethrough, preferably radially symmetrically distributed about the periphery of the valve guide 86 as seen in FIG. 4. Corresponding to each perforation 88 in the valve guide 86 is a depression 90 in the gasket 44. At the bottom of depression 90, there remains a thin, resilient diaphragm 92. Depending upon the thickness and elasticity of the gasket 44, and the dimensions of the valve chamber 82, the depression 90 may comprise different depths or be eliminated entirely as will be appreciated by one of skill in the art.

Disposed within or coaxially above each perforation 88 is a piston 94. Piston 94 is capable of axial reciprocating movement between a first open position and a second closed position. When in the open position, in which the diaphragm 92 is relatively planar, fluid in the flow channel 80, formed between the base 37 and the gasket 44, flows freely across the valve chamber 82 and into the drain 84. When the piston 94 is forced axially downwardly into the second position by lower cam surface 96 on knob 108, which will be discussed, the piston 94 extends through the perforation 88 and elastically deforms the diaphragm 92 in such a manner as to occlude the corresponding valve chamber 82, thereby preventing passage of fluid therethrough. To facilitate the sealing function, the terminal end 98 of the piston 94 and the bottom of valve chamber 82 can be provided with complementary surface configurations.

In an alternate embodiment (not illustrated), the valve chambers 82 and fluid passageways 80 and 84 are formed into the bottom side of the gasket 44. This embodiment will operate in substantially the same way as the foregoing embodiment, as will be appreciated by one of skill in the art.

Although each of the plurality of pistons 94 can be individually formed and mounted in the flow regulator 22, or take the form of spherical beads in a race, it is convenient to mold them into a unitary structure such as that illustrated in FIG. 4. In this embodiment, each of the plurality of pistons 9 is radially symmetrically spaced about a central hub 100 and secured thereto by means of a resilient arm 102. Each piston 94 comprises a substantially tubular body terminating at its terminal end 98 in a conical taper to enhance the seal formed between the diaphragm 92 and the valve chamber 82.

At its upper end, each piston is provided with a radially outwardly extending annular collar 104. The collar 104 functions to provide an enlarged upper surface 106 for slidably engaging the lower surface of a rotatable annular cam 96 which may be rotationally positioned by a selector knob 108. The lower cam surface 96 of selector knob 108 contains a recess 110 for receiving any one of the plurality of the surfaces 106.

When assembled, the lower surface of the cam 96 bears down upon each of the pistons 94, thereby closing the corresponding valves, except for a piston 94 which is radially aligned with recess 110. The resilient property of the diaphragm 92 together with that contributed by the resilient arm 102, if used, operate to provide an upward bias of each piston 94 against lower cam surface 96. With regard to any piston 94 which is rotationally aligned with recess 110, the upward bias is sufficient to move that piston into the "open" position with the collar 104 disposed within recess 110. In this manner, the corresponding diaphragm 92 will resume its unstressed state and the corresponding valve chamber 82 will freely permit the passage of fluid from flow channel 80 into drain 84. All other pistons will be in the "closed" position due to the cam 96.

Fluid which has traversed the control wafer 46 and an open valve chamber 82 is collected in the common drain line 84 of base 37, flows via an effluent path 38a formed in base 37 and then is forced through the effluent port 50 (See FIG. 3) into the effluent channel 38. From there, the fluid is conducted via IV line 25 to the patient.

By rotating knob 108, any one selected valve may be opened, while maintaining all of the remaining valves closed. In this manner, any given one of the preselected lengths of the capillary tube in the control wafer can be selected. Since the effective length of the capillary tube is the rate regulating step, any of a plurality of predetermined flow rates may be selected, such as from within a range of from 1 milliliter or less per hour at the low rate end to 100 milliliters or more per hour at the high flow rate end of the range. For example, one flow regulator in accordance with the present invention exhibited flow rates of approximately 2.08, 4.17, 6.25, 12.5, 25, 50 and 100 milliliters per hour.

The selector knob 108 is provided with coil spring 101 which has a tangentially projecting arm 103. The spring 101 is rotationally secured to the interior of the selector knob 108 (See FIG. 3) with the arm 103 extending radially outwardly into the annular recess 105 in the underside of annular flange 109. The recess 105 is provided with radially inwardly extending teeth (not illustrated) into which the arm 103 is biased, so that the knob 108, when rotated, will distinctly snap from one position to the next.

Although this invention has been described in terms of certain preferred embodiments, other embodiments that are apparent to those of skill in the art are also within the scope of this invention. Accordingly, the scope of the invention is intended to be defined only by reference to the appended claims.

I claim:

1. A flow controller for regulating the rate of flow from a source of fluid under pressure, comprising:
   (a) a housing having an influent, effluent port, and fluid flow path therebetween;
   (b) a flow restriction channel in the flow path, for regulating the rate of flow, said restriction channel having an influent end and at least two effluent apertures along its length;
   (c) a valve in the housing associated with each of the apertures along the flow path; and
   (d) a single control for selectively opening any one of the valves and maintaining each additional valve closed;
   wherein the opening of any one of the valves places in the influent port in fluid communication with effluent port by way of the a unique length of flow restriction channels associated with the open valve.

2. A flow controller as in claim 1, wherein the valve comprises a fluid passageway having a movable wall, and means of compressing the wall to prevent flow through the passageway.

3. A flow controller as in claim 2, wherein the fluid passageway is enlarged in cross-sectional dimension in the area of the valve to form a valve chamber for receiving the movable wall.

4. A flow controller as in claim 2, wherein the movable wall comprises a flexible elastomeric material.

5. A flow controller as in claim 4, wherein the fluid passageway comprises a groove formed on the surface of the housing, and an elastomeric gasket for enclosing the grooves to form a fluid passageway.

6. A flow regulator, comprising:
   (a) a first plate having a flow channel on the surface thereof;
   (b) a second plate, secured to the surface of the first plate and enclosing the flow channel to form a chip having a capillary tube therethrough;
   (c) an influent port on the chip, in fluid communication with the capillary tube; and
   (d) a plurality of effluent apertures on the chip, each in fluid communication with the capillary tube at a different distance along its length from the influent port.

7. A flow controller for regulating the rate of flow from a source of fluid under pressure, comprising:
   (a) a housing having an influent port, an effluent port, and a fluid flow path therebetween;
   (b) a plurality of flow restriction channels in the flow path, for regulating the rate of flow;
   (c) a plurality of normally closed valves in the housing, each valve associated with a different flow restriction channel; and
   (d) a single control, for selectively opening any one of the valves;
   wherein opening any of the valves places the influent port in fluid communication with the effluent port by way of a unique flow restriction channel associated with the open valve.

8. A flow controller as in claim 7, wherein the flow restriction channels are formed on the surface of a silicon wafer.

9. A variable rate fluid flow controller for providing a predetermined delivery rate from a pressurized source of fluid medication, comprising:
   (a) a housing having an influent port, an effluent port and at least two predetermined capillary flow paths therebetween such that each flow path has a different predetermined capillary length to provide a predetermined flow rate between the inlet port and the outlet port.

(b) at least two pinch valves in the housing, each pinch valve associated with one of said capillary flow paths; and (c) a movable cam for selectively opening and closing the pinch valves.

10. A variable flow controller as in claim 9, wherein the flow paths are disposed in a series relationship between the influent and effluent ports.

11. A variable flow controller as in claim 9, wherein the flow paths are disposed in a parallel relationship between the influent and effluent ports.

12. A variable flow controller as in claim 9, wherein the flow paths comprise a length of flow restriction tubing having at least two effluent apertures thereon.

13. A variable flow controller as in claim 9, wherein the cam permits opening of any one of the pinch valves while maintaining all other pinch valves closed.

14. A variable flow controller as in claim 9, wherein each flow path comprises a flexible diaphragm which is compressed by the cam to prevent fluid flow through the flow path.

15. A variable flow controller as in claim 14, wherein the cam is rotatable.

16. A variable flow controller as in claim 15, further comprising a piston associated with each valve, the piston movable from a first position in which fluid is permitted to flow through the valve and a second position in which the flexible diaphragm is compressed to prevent fluid flow through the valve, the piston movable from the first to the second position in response to the rotational position of the cam.

17. A flow controller for regulating the rate of flow from a source of fluid under pressure, comprising:

(a) a housing having an influent port, an effluent port and a fluid flow path therebetween;

(b) a plurality of flow restriction channels in a series relationship along the flow path, for regulating the rate of flow;

(c) a plurality of normally closed valves in the housing, each associated with a different flow restriction channel; and (d) a single control for selectively opening at least one of the valves; wherein opening any one of the valves places in the influent port in fluid communication with the effluent port by way of a unique flow restriction channel associated with the open valve.

* * * * *

UNITED STATES PATENT AND TRADEMARK OFFICE
CERTIFICATE OF CORRECTION

PATENT NO. : 5,009,251

DATED : April 23, 1991

INVENTOR(S) : Pike, et al

It is certified that error appears in the above-identified patent and that said Letters Patent is hereby corrected as shown below:

Column 10, line, "pistons 9" should read --pistons 94--.

Signed and Sealed this

Ninth Day of March, 1993

Attest:

STEPHEN G. KUNIN

Attesting Officer

Acting Commissioner of Patents and Trademarks